United States Patent

Lin et al.

[11] Patent Number: 5,832,410
[45] Date of Patent: Nov. 3, 1998

[54] METHOD OF USING A COMPUTER TO COLLECT CHEMICAL SIGNALS DIRECTLY

[76] Inventors: Shengfu Lin, 3F, 7, Lane 110, Chien-Kang Street, Taipei, Taiwan; Chih-I Lin, 14292 Spring Vista La., Chino Hills, Calif. 91709

[21] Appl. No.: 873,241

[22] Filed: Jun. 11, 1997

Related U.S. Application Data

[63] Continuation of Ser. No. 354,031, Dec. 6, 1994, Pat. No. 5,644,501.

[51] Int. Cl.$^6$ .................................................. G01N 27/26
[52] U.S. Cl. ............................... 702/22; 702/30; 702/32; 204/407; 204/400; 204/406
[58] Field of Search ..................... 364/496–500, 364/550, 551.01, 509, 510, 528.01; 204/400, 401, 409, 405–407, 556, 403; 422/68.1, 81, 62, 119, 83, 98, 82.01, 82.02; 340/632; 324/464, 465, 468, 438, 450; 73/23.36; 382/313; 210/614; 702/22–25, 30–32

[56] References Cited

U.S. PATENT DOCUMENTS

4,547,735  10/1985  Kiesewetter et al. .................... 324/450
4,972,099  11/1990  Amano et al. ........................... 382/313
5,106,511   4/1992  Kodukula ................................. 210/614
5,128,015   7/1992  Szuminsky et al. ..................... 204/403
5,198,774   3/1993  Williams, II et al. .................. 324/468
5,268,852  12/1993  Forsythe et al. ........................ 324/438
5,382,331   1/1995  Banks ...................................... 204/407
5,423,963   6/1995  Fletcher et al. ......................... 204/401
5,526,280   6/1996  Consadori et al. ........................ 422/98
5,597,534   1/1997  Kaiser .................................. 422/82.02
5,654,497   8/1997  Hoffheins et al. ....................... 364/498

Primary Examiner—Emanuel Todd Voeltz
Assistant Examiner—Hal P. Wachsman
Attorney, Agent, or Firm—Bacon & Thomas, PLLC

[57] ABSTRACT

The present invention relates to a method of using a computer to collect chemical signals directly from a chemical sensor. This method first converts output signals received from the chemical sensor into digital signals by using a transforming circuit and an analog-to-digital converter in cooperation with a control computer program executed in the computer; transfers the digital signals to the computer and processes the digital signals in the computer in accordance with the type of the chemical sensor used.

10 Claims, 4 Drawing Sheets

METHOD OF USING A COMPUTER TO COLLECT CHEMICAL SIGNALS DIRECTLY

This application is a continuation of U.S. application Ser. No. 08/354,031, filed Dec. 6, 1994 now U.S. Pat. No. 5,644,501, issued Jul. 1, 1997.

FIELD OF THE INVENTION

The present invention is related to a method of using a computer to collect chemical signals directly.

BACKGROUND OF THE INVENTION

There are three types of chemical sensors: chemical sensors used in conductometry, chemical sensors used in amperometry and chemical sensors used in potentiometry. For example pH electrodes, ion-selective electrodes, ISFET (ion-selective field effect transistors), enzyme electrodes, biosensors, etc. are widely used in chemical, biochemical, biotechnological, environmental protection and medical analyzers such as a pH-meter, ion analyzer, polarography, chemical analyzer, bioanalyzer, bioreactor, ion chromatography, flow-injection analyzer, etc. Moreover, Chemical sensors are used in quality control analysis, on-line analysis and monitor-control apparatus for chemical manufacturing processes. U.S. Pat. No. 4,897,128 discloses a method of controlling the ionic concentrations of reactants in a zinc phosphate coating sink by using pH-electrodes and fluorine-ion selective electrodes.

A chemical sensor can convert a specific chemical signal (i.e. concentration of a certain component of a sample) or the sum of many chemical signals into an electronic signal such as electric potential, resistance, or current. However, in order for the users to understand the physical meanings of a chemical signal, this electronic signal still needs to be further processed, stored, and/or displayed by an signal processing equipment. For example, a pH-electrode has to be incorporated with a pH meter to determine the pH value of a solution. Similar requirements applies to the usage of a chemical analyzer, and pH monitor control equipment. A chemical sensor for amperometry can determine the reaction current in the potential static condition by relying on a potentiostat, and then indirectly obtain the concentration of a specific specie. Similar requirement applies to the usage of a chemical analyzer and a biochemical analyzer. A chemical sensor for conductometry can determine the conductivity by relying on a conductometer, and the determined conductivity can then be used to indicate the ending of a conductometric titration, or used as the standards of ionic concentrations in ion chromatography. Each of these kinds of signal processing equipment has a specific usage, and cannot be exchanged for use in another chemical sensor. For example, a pH-meter can not be used as a conductometer or a coulometer, and it also can not be extended to another use. Without a special design, a potentiometer cannot be extended to be used in potentiostatic coulometry.

Generally speaking, conventional signal processing equipment can be divided into 4 categories. The first category includes the simple instruments which cannot be connected to a computer or a recorder. For example, pH-meters (types 704, 620, 588) of Metrohm, Switzerland, do not have very powerful functions, and do not have the ability to execute data communication with other instruments like chemical analyzers.

The second type of signal processing equipment, however, cannot be connected with a computer externally, but is able to communicate with an external recorder through its analog signal output node, and, therefore, enhance its function. Examples are the pH-meter (PHM82) of Radiometer, Denmark, and the Potentio/Galvanostat and Coulomb/Amperohour Meter of Nichia, Japan. The functions of these signal processing equipment are still limited. Although an analog signal output node is available, it is still physically difficult to execute data communication with other instruments.

The third type of signal processing equipment cannot be externally connected with either a computer or a recorder, but, has its own built-in display and printer. Examples are the modular biological fluid analyzer disclosed in U.S. Design Pat. No. D330,770, and a clinical chemistry analyzer disclosed in U.S. Design Pat. No. D332,314. These built-in functions clearly can not be compared with those of a computer. For example, the resolution of a computer monitor is better than a built-in display of a signal processing equipment. A computer also has superior data processing/storing capabilities and various accessories which can be mounted into the computer easily. Moreover, the analyses and data processing functions of this type of signal processing instruments cannot be extended or enhanced.

The fourth type of signal processing equipment can be connected with a computer externally in order to enhance its data processing/storing/display ability. Examples include the voltammetry Model 693 VA Processor from Metrohm, Switzerland; the PHM 85 pH-meter from Radiometer, Denmark; the Potentiostat/Galvanostat Model 273A from EG&G, U.S.A.; a chemical analyzer disclosed in U.S. Pat. No. 4,935,875; and the on-line biological inhibition/toxicity detector disclosed in U.S. Pat. No. 5,106,511. This type of signal processing equipment contains a central processing unit. For example, line 17, column 5 of U.S. Pat. No. 5,106,511 and line 45, column 6 of U.S. Pat. No. 4,935,875 state that these signal processing equipment use a Model 6809 microprocessor (Motorola, U.S.A.), ROM, RAM, timer, display or monitor, keyboard or I/O port, Analog-to-Digital converter (ADC), etc. (For further details, please refer to FIG. 1 of U.S. Pat. No. 4,935,875 and its explanation.) In addition, when these signal processing equipment are to be connected externally with computers, RS-232 or GPIB cards need to be used as the medium for data communication.

In order to extend the analysis and data processing functions, the inventors have focused their research on the structure of the fourth type of signal processing equipment. The result is that except for some minor components such as ADC, the primary components such as CPU, ROM, RAM, timer, monitor, keyboard, I/O port, printer and disk drive, are all included in a computer. This is advantageous because the primary components of a computer are generally more powerful and more compatible to external accessories than the built-in components in the fourth type of signal processing equipment. Therefore, the fourth type of signal processing equipment may essentially be replaced by a computer. In addition, the minor components such as ADC can be easily purchased in the market. Accordingly, it is possible to use an ADC bought from the market to directly convert the analog signals from a chemical sensor into digital signals, and transfer the digital signals to a computer where they are processed. If this can be accomplished, the signal processing equipment used at the present time can be entirely replaced by a computer with modifications. Nowadays, some mechanical-sensors or thermal sensors are using the same idea of replacing signal processing equipment with computers and ADCs. However, this idea has not been used in chemical sensors.

Based on the above analyses, the inventors used a market-purchased ADC to connect a chemical sensor which is used in potentiometry (e.g. a pH electrode) and a computer. In other words, the output signals from a chemical sensor were received in a series as follows: "chemical sensor→ADC→computer". However, the results showed that although a large number of data were collected, the average value of these data could not represent the actual value accurately because the average values were not consistent for several runs repeated by the same procedures. The deviations were large and no pattern could be found.

After more intensive research, the inventors found out that the addition of a voltage follower could solve the existing problem. That is to say, if the connection is in a series of "chemical sensor→voltage follower→ADC→computer", the output signals of a chemical sensor which is used in potentiometry can be easily and accurately obtained.

Furthermore, current ADCs in the market often have an additional function of Digital-to-Analog Conversion (DAC) at the same time. Therefore, it is theoretically possible to use a DAC to convert the digital signals sent by a computer into analog signals, and therefore use a chemical sensor to execute voltammetry method; or under potentiostatic conditions, to excute amperometry and obtain a concentration of a certain component of a sample. The actual experimental results showed that although the voltage output of the DAC was stationary, the electric potential of the working electrode was fluctuating. However, this problem can be solved by the addition of a potentiostat circuit. Similarly, a Galvanostat circuit can be used to solve the same problem in potentiometry under Galvanostatic conditions.

In the conventional signal processing equipment of a the chemical sensor used in conductometry, a transducer has to be added to reduce the voltage of an alternating current source for the conductance cell. However, the inventors found that by executing a control program in the computer, the DAC can be used as an alternating current source.

SUMMARY OF THE INVENTION

Based on the above discoveries, the present inventors disclose a system for carrying out amperometry, potentiometry, conductometry, and voltammetry for chemical sensors of different types, which comprises a computer, an ADC/DAC, a voltage follower, a current-potential converter, a potentiostat circuit, a Galvanostat circuit and a proper computer program which can be executed in said computer. In other words, the invention provides a method and system having the combined functions of a pH meter, an amperometer, a conductometer, a potentiostat/Galvanostat, and a voltammetric processor, and thereby substantially covers all equipment which use chemical sensors or any extension uses of these equipment, e.g. as a conductometer used in ion-chromatography. In contrast, the conventional signal processing equipment for chemical sensors have their own specific usages that cannot be exchanged. For example, a pH meter can be used only as a pH meter, not a potentiostat, and a voltammetric processor can not be used as a conductometer at the same time.

In addition, because ADC/DAC cards on the market usually have DIO (digital input/output) functions, and hence they can also be used as the control of a pump or a valve, the system described above can generally be connected with other accessories (if necessary) to be used as a chemical analyzer, bio-chemical analyzer, clinic analyzer, pH/electric potential/conductance automatic titration meter, ion chromatography, polarography, and a quality control, on-line analysis and monitor-control equipment of a chemical manufacturing process.

The first objective of this invention is to provide a method of converting output signals of a chemical sensor into digital signals and processing said digital signals by using a computer.

The second objective of this invention is to provide a system for collecting chemical signals from a chemical sensor, which includes a computer, an ADC, a transforming circuit and a proper computer program which can be executed in said computer.

The third objective of this invention is to provide a system for collecting chemical signals from a chemical sensor, which includes a computer, ADC/DAC/DIO interface cards, a transforming circuit and a proper computer program which can be executed in the computer.

BRIEF DESCRIPTION OF THE DRAWINGS

The foregoing and other objects, aspects and advantages will be better understood from the following detailed description of the preferred embodiments of the invention with reference to the accompanying drawings wherein like numerals represent like elements and in which.

DETAILED DESCRIPTION OF THE INVENTION present invention is related to a method of using a computer to collect chemical signals directly from a chemical sensor, in which said computer is provided with an Analog-to-Digital converter (ADC) and said chemical sensor is connected to said ADC with a transforming circuit. The present method includes the following steps:

converting output signals received from said chemical sensor into digital signals by using said transforming circuit and said ADC in cooperation with a control computer program executed in said computer;

transferring said digital signals from said ADC to said computer; and processing said digital signals in said computer in accordance with the type of said chemical sensor.

When the chemical sensor used in the present method is for potentiometry, said transforming circuit is a voltage follower. In addition, said computer may be further provided with a Digital-to-Analog converter (DAC), and said DAC is connected to said chemical sensor with a Galvanostat circuit, wherein a Galvanostatic current is received by said chemical sensor from said Galvanostat circuit in cooperation with said DAC and said control computer program executed said computer so that a potentiometry under Galvanostatic condition is carried out.

When the chemical sensor used in the present invention is for amperometry, said transforming circuit is a current-potential converter. In addition, said computer may be further provided with a Digital-to-Analog converter (DAC), and said DAC is connected to said chemical sensor with a potentiostat circuit, wherein a current having a desired electric potential wave form or a potentiostatic current is received by said chemical sensor from said potentiostat circuit in cooperation with said DAC and said control computer program executed by said computer so that a voltammetry or an amperometry under potentiostatic condition are carried out.

When the chemical sensor used in the present invention is for conductometry, said transforming circuit is a current-potential converter, and said computer is further provided with a Digital-to-Analog converter (DAC) which is connected to said chemical sensor, wherein an alternating current is received by said chemical sensor from said DAC in cooperation with said control computer program executed said computer so that a conductometry is carried out.

The chemical sensor can be a sensor array. In Chapter 6 entitled "Multi-Component analysis in Chemical Sensing", Vol. 2 entitled "Chemical and Biochemical Sensors", of *Sensors* (edited by W. Gopel, I. Hesse and J. N. Zemel, and published by VCH company, Germany), a signal sensor, a sensor array, and the combination of both are demonstrated. The chemical sensors described here are general chemical sensors, including common biosensors, biochemical sensors, enzyme electrodes, gas sensors, etc. The form of these chemical sensors can be a probe, an electrochemical sensor, a liquid electrolyte sensor, a solid state electrochemical sensor, a field effect chemical sensor, a calorimetric chemical sensor, an optochemical sensor, a piezoelectrically chemical sensor, etc. These sensors are described in Chapters 1, 5, 7, 8, 9, 10, 11, 12, 13, 14 and 16, Vols. 2 and 3 of *Sensors* (edited by W. Gopel, I. Hesse and J. N. Zemel, and published by VCH company, Germany), which can convert chemical signals into electronic signals.

The voltage follower described above is a known circuit. Please refer to *Microelectronics*, Jacob Millman and Arvin Garbel, second edition, p. 445. This voltage follower is used in this invention to convert the high impedance electronic signals of the chemical sensors described above to medium or low impedance signals. Generally, the output electronic signals of a chemical sensor are high impedance electronic signals of about $10^5$–$10^6$ Ohms. If these signals are connected with an ADC directly, the ADC cannot convert the analog signals into digital signals accurately. However, if a voltage follower is inserted between a chemical sensor and an ADC, the problem will be solved.

The Galvanostat circuit is a known circuit and is described in *Principles of Instrumental Analysis*, Dougls A. Skoog, third edition, p. 49.

Said current-potential converter is a known circuit. Please refer to *Microelectronics*, Jacob Millman and Arvin Garbel, second edition, pp. 449–450. This current-potential converter can convert the electric current signals of a chemical sensor used in amperometry into voltage signals, in order for the ADC to convert this analog voltage signals into digital signals.

The potentiostat circuit is a known circuit. Please refer to *Principles of Instrumental Analysis*, Douglas A. Skoog, p. 49. This potentiostat circuit can equalize the electric potential output of a DAC and the voltage of the working electrode of the chemical sensor. In other words, the voltage of the working electrode is constant. If the DAC is connected to a chemical sensor, the voltage output of the DAC, V, and the voltage of the working electrode of the chemical sensor, $V_1$, has the following relationship:

$$V = V_1 + V_2 + IR + V_3 + V_4$$

$V_1$ stands for the voltage of the counter electrode, IR stands for the IR drop caused by current-resistance, and $V_3$ and $V_4$ are the overvoltage of the working electrode and counter electrode, respectively. Because $V_3$, $V_4$ are related to the complex kinetic polarization and concentration polarization, the voltage of the working electrode is not stable even though the DAC output voltage (V) is constant. During an electrochemical analysis, it is required that the voltage of the working electrode remains constant. Therefore, a potentiostat circuit has to be inserted between the DAC and the chemical sensor to solve the problem.

Each of the voltage follower, current-potential converter, potentiostat circuits and/or Galvanostat circuit described above is a simple circuit. When necessary, they can be combined to be in one circuit board, or even made into a computer serial port card, or be included in an ADC interface card. The ADC described above is a known circuit. Some ADC interface cards on the market, in addition to ADC, have DAC and DIO functions in one interface card. For example, the PCL-718, PCL-818, PCL-812, PCL-812PG interface cards manufactured by Advantech Co. Ltd., Taiwan all have 16 channels ADC, 16 DI (digital inputs), 16 DO (digital outputs) and 1–2 channels DAC. In each of these ADC interface cards described above, the DAC and/or DIO channels can also be formed in a separate interface card. Moreover, remote sensor-to-computer interface modules such as ADAM 4000 series manufactured by Advantech Co. Ltd., Taiwan may be used as the ADC of the present invention so that said output signals of said chemical sensor can be collected by a remote computer.

The computer described above can be a desktop computer (a PC or a minicomputer), or a portable computer (notebook or laptop computer), preferably a desktop PC or a notebook computer.

The control computer program can be stored as a firmware or a software which can be read and executed by the computer, and preferably as software due to software's flexibility of editing and change.

A system for collecting chemical signals disclosed by the present invention comprises:

a computer for executing a control computer program;

one or more chemical sensors for providing output signals;

one or more transforming circuits for transforming said output signals received from said one or more chemical sensors into desired electronic signals, one end of said one or more transforming circuits being connected with said one or more chemical sensors;

one or more Analog-to-Digital Converter (ADC) interface cards for converting said desired electronic signals into digital signals and transferring said digital signal to said computer, which connects the other end of said one or more transforming circuit with the computer;

in which said one or more transforming circuits are a voltage follower provided that said one or more chemical sensors are the chemical sensor used in potentiometry; and/or said one or more transforming circuits are a current-potential converter provided that said one or more chemical sensors are the chemical sensor used in amperometry or conductometry, whereby said output signals from said chemical sensor are converted into digital signals by using said transforming circuit and said ADC in cooperation with said control computer program executed in said computer, and said digital signals are processed in said computer in accordance with the type of said chemical sensor.

When said one or more chemical sensors are the chemical sensor used in potentiometry, said computer is further provided with a Digital-to-Analog converter (DAC), and said DAC is connected to said one or more chemical sensors with a Galvanostat circuit so that a Galvanostatic current can be received by said one or more chemical sensors from said Galvanostat circuit in cooperation with said DAC and said control computer program executed in said computer, and thus a potentiometry under Galvanostatic condition can be carried out.

When said one or more chemical sensors are the chemical sensor used in amperometry, said computer is further provided with a Digital-to-Analog converter (DAC), and said DAC is connected to one or more chemical sensors with a potentiostat circuit so that a current having a desired electric potential wave form or a potentiostatic current can be received by said one or more chemical sensors from said potentiostat circuit in cooperation with said DAC and said control computer program executed in said computer, and thus a voltammetry or an amperometry under potentiostatic condition can be carried out.

When said one or more chemical sensors are the chemical sensor used in conductometry, said computer is further provided with a Digital-to-Analog converter (DAC) which is connected to said one or more chemical sensors so that an alternating current can be received by said one or more chemical sensors from said DAC in cooperation with said control computer program executed in said computer, and thus a conductometry can be carried out.

The function of this system entirely depends on a control computer program executed by the computer.

The computer, ADC interface card, chemical sensor, voltage follower, current-potential converter, potentiostat circuit and Galvanostat circuit contained in the system are the same as those described above in connection with the method of using a computer to collect chemical signals from a chemical sensor directly.

The one or more ADC interface cards can be connected with the computer by inserting gold contacts provided on said one or more ADC interface cards into one or more slots provided by the computer or expanded therefrom.

Preferably, the one or more ADC interface cards can further have digital-to-analog converter (DAC) and digital input/output (DIO) functions.

Generally, the system described above can be connected with other accessories (if necessary) to be used as a chemical analyzer, bio-chemical analyzer, clinic analyzer, pH/electric potential/conductance automatic titration meter, ion chromatography, polarography, and a quality control, on-line analysis and monitor-control equipment of a chemical manufacturing process.

To further explain this invention, several preferred embodiments will be described in the following text by referring to the accompanying figures.

Figure 1:
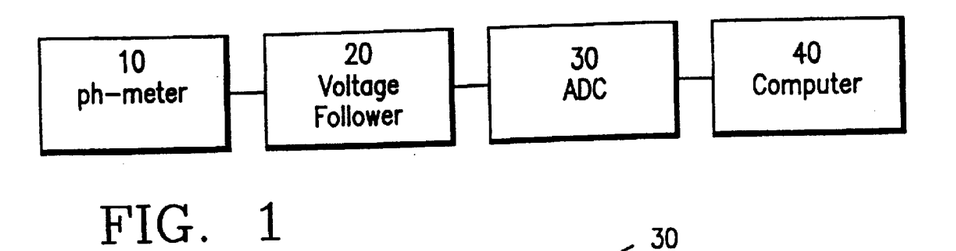
FIG. 1 is a block diagram which shows a system for collecting chemical signals from a chemical sensor according to a first preferred embodiment of the present invention.

FIG. 1 is a block diagram which shows a system for collecting chemical signals from a chemical sensor according to a first preferred embodiment of the present invention, wherein the chemical sensor 10 are connected to an ADC 30 with a voltage follower 20, and said ADC 30 is connected to a computer 40.

Figure 2:
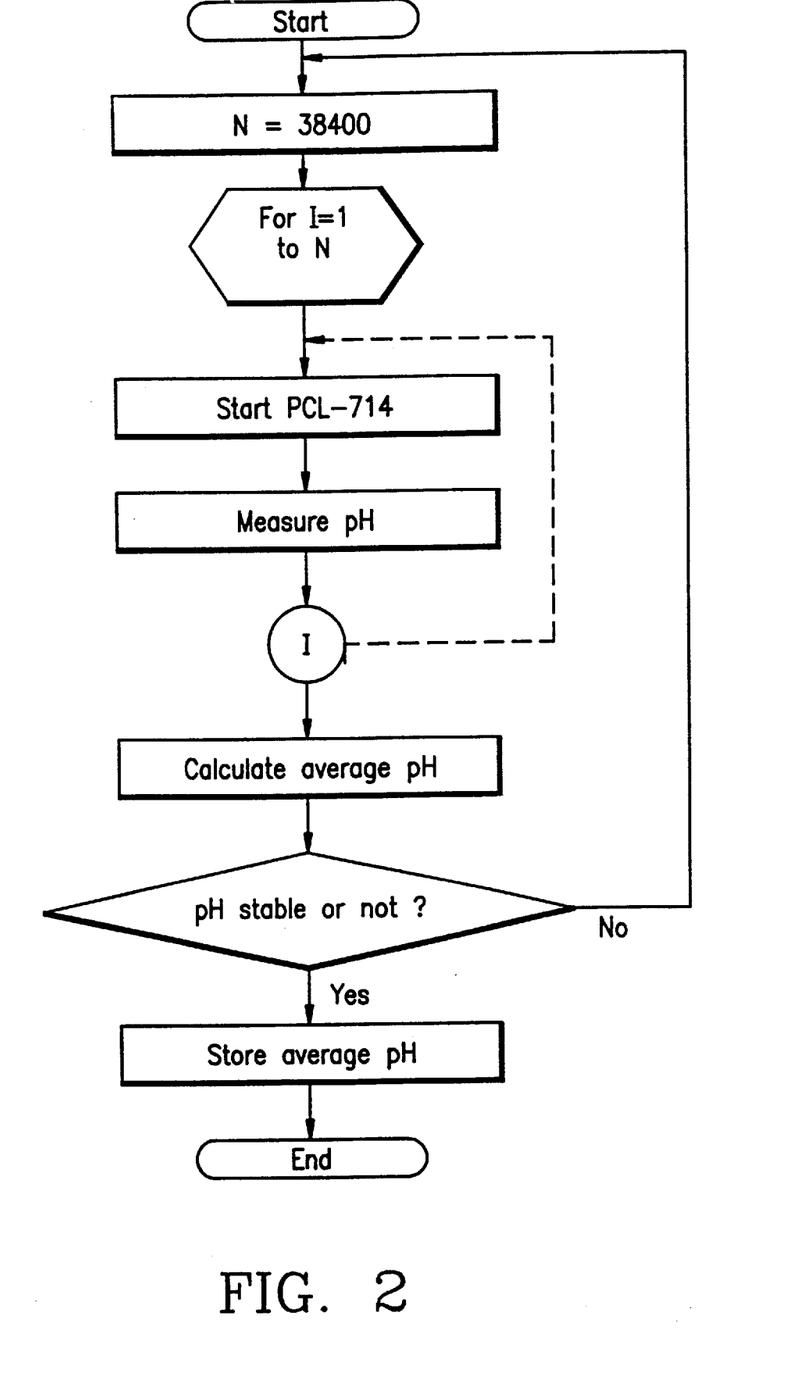
FIG. 2 is a flow chart of a control computer program to be executed in the computer in FIG. 1 when the chemical sensor thereof is a pH meter.

FIG. 2 is a flow chart of a control computer program to be executed in the computer of FIG. 1 when the chemical sensor thereof is a pH meter, in which the ADC/DAC is manufactured by Advantech Co. Ltd., Taiwan (model PCL-714). The experiment data collected are shown in the following Example 1.

Figure 3:
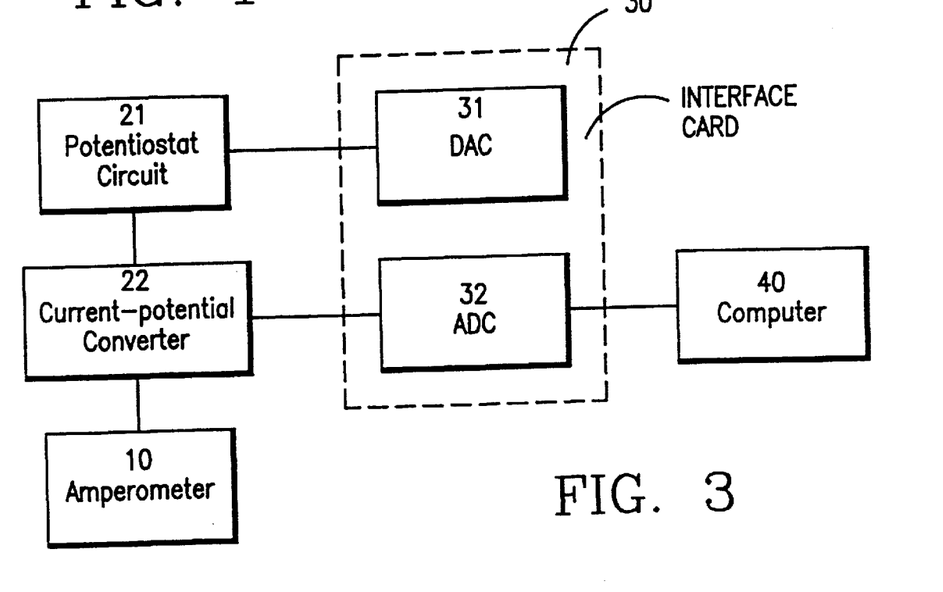
FIG. 3 is a block diagram which shows a system for collecting chemical signals from a chemical sensor according to a second preferred embodiment of the present invention.

FIG. 3 is a block diagram which shows a system for collecting chemical signals from a chemical sensor according to a second preferred embodiment of the present invention, in which 10 stands for the chemical sensor used in amperometry, 21 stands for a potentiostat circuit, 22 stands for a current-potential converter, 30 stands for an interface card, 31 stands for DAC in the interface card, 32 stands for ADC in the interface card, and 40 stands for a computer. DAC 31 gives a specific electric potential to the potentiostat circuit 21 to execute potentiostatic electrolysis, cyclic voltammetry or square wave voltammetry. The current formed in the chemical sensor 10 is converted into voltage signals by current-potential converter 22, and the voltage signals are converted to digital signals by ADC 32, which are then processed by the computer 40. This system can be used in amperometry under potentiostatic condition or voltammetry like polarography.

Figure 4:
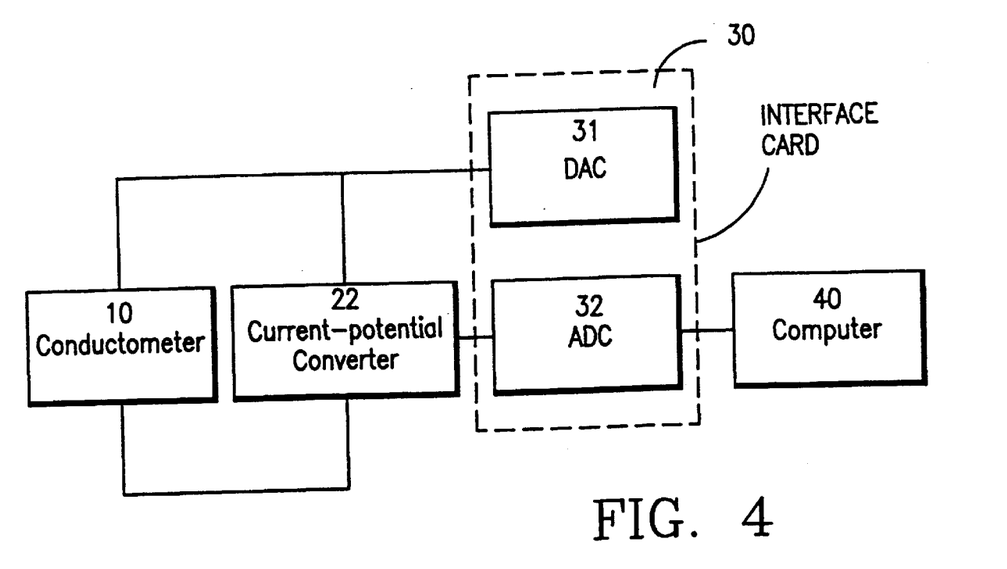
FIG. 4 is a block diagram which shows a system for collecting chemical signals from a chemical sensor according to a third preferred embodiment of the present invention.

FIG. 4 is a block diagram which shows a system for collecting chemical signals from a chemical sensor according to a third preferred embodiment of the present invention, in which the numbers 22, 30, 31, 32 and 40 represent the same elements represented by the like numbers in FIG. 3, and 10 represents a chemical sensor for conductometry. DAC 31 gives an electric potential of sine wave to the chemical sensor 10. The resultant current, through the current-potential converter 22 is converted to resistance signals, which are then measured by ADC 32. This system can be used in conductometry.

EXAMPLE 1

Figure 6:
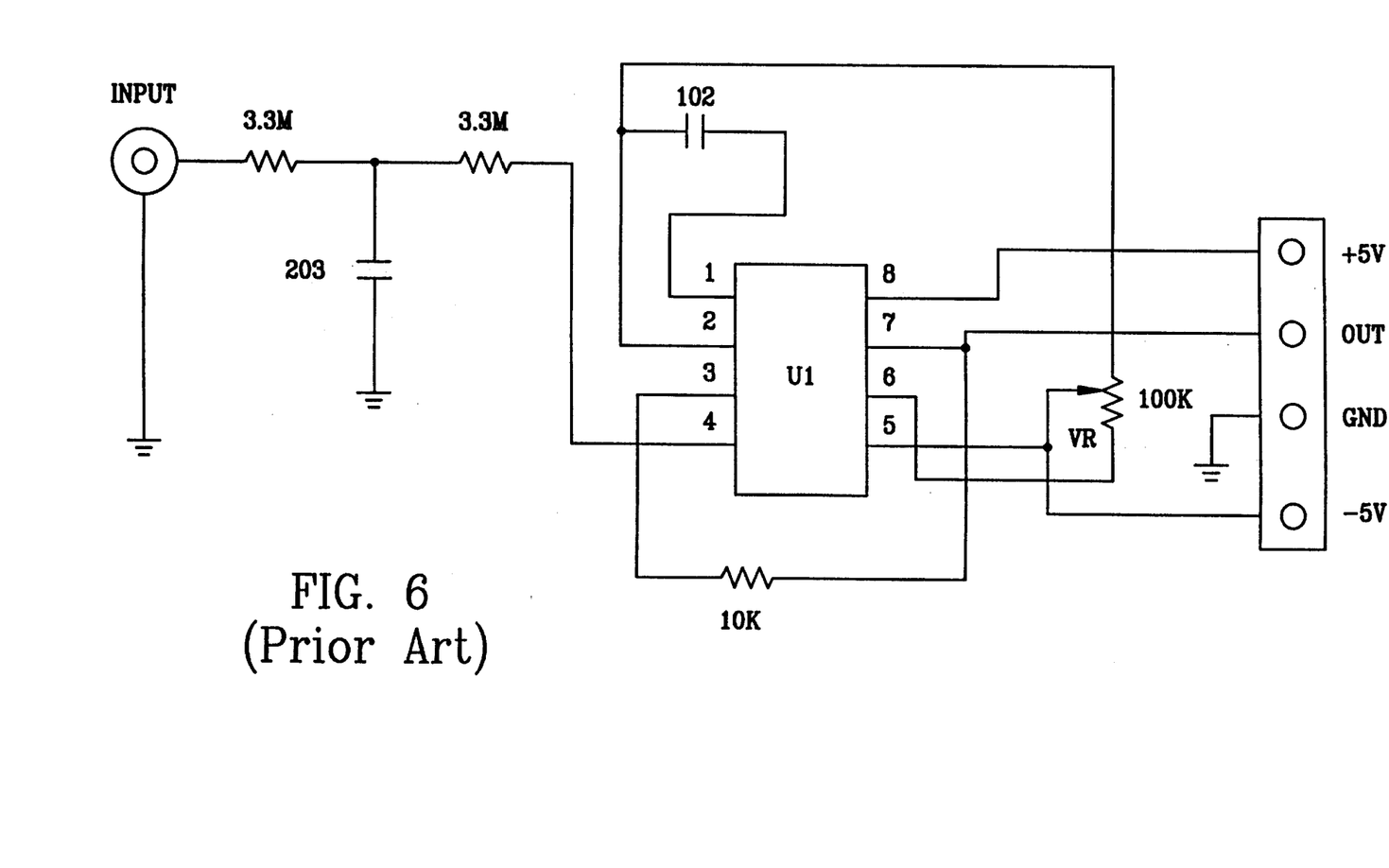
FIG. 6 is an electric circuit of a voltage follower, wherein an IC U1 is sold by Fujitsu Co., Japan under a code of OP41, FJ9201.

The system shown in FIG. 1 was used to measure pH value of an aqueous buffer solution prepared by mixing 1:1 (v/v) of 0.1M acetic acid solution and 0.1M sodium acetate solution. A pH electrode Model PHM82 purchased from Radiometer, Denmark, was used as the chemical sensor 10; the circuit shown in FIG. 6 was used as the voltage follower 20; an IBM compatible AT computer was used as the computer 40; a PCL-714 ADC/DAC interface card purchased from Advantech Co. Ltd., Taiwan was used as the ADC 30 in FIG. 1. 174 average pH values were obtained, each of which was obtained by recording about 30 thousand measurements (1–2 seconds measuring time) and calculating the average value of the about 30 thousand measurements. The results are shown as follows:

| Average pH | Appearing times | Accumulation of appearing times |
|---|---|---|
| 4.6287 | 2 | 2 |
| 4.6288 | 17 | 19 (2 + 7) |
| 4.6289 | 22 | 41 (19 + 22) |
| 4.6290 | 54 | 95 (41 + 54) |
| 4.6291 | 41 | 136 (95 + 41) |
| 4.6292 | 23 | 159 (136 + 23) |
| 4.6293 | 12 | 171 (159 + 12) |
| 4.6294 | 1 | 172 (471 + 1) |
| 4.6295 | 2 | 174 (172 + 2) |

Figure 5:
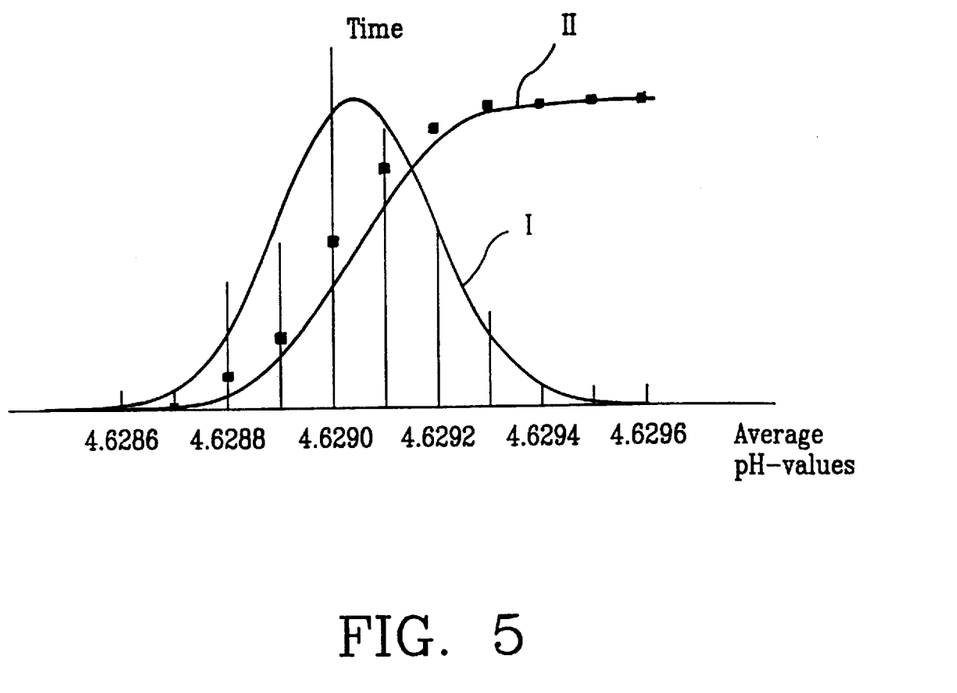
FIG. 5 is a plot which shows a pH value distribution of acetic acid/sodium acetate buffer solution measured by using the system in FIG. 1 and the algorithm in FIG. 2.

Two curves (normal distribution and accumulation distribution) were made according to the above data, as shown in FIG. 5. In FIG. 5, the horizontal axis stands for the average pH values. The vertical line at each average pH value represents the number of times an average pH value appears; the * at each average pH value represents the accumulation of the appearing times of average pH values less than or equal to the average pH value. It can be seen from FIG. 5 that the distribution of experimental data fits the theoretical distribution represented by curves I and II. The standard deviation is 0.0002.

What is claimed is:

1. A method of using a computer to collect chemical signals directly from a chemical sensor, in which said computer is provided with an Analog-to-Digital converter (ADC) and said chemical sensor is connected to said ADC with a transforming circuit, said method comprising the following steps:

converting output signals received from said chemical sensor into digital signals by using said transforming circuit and said ADC in cooperation with a control computer program executed in said computer;

transferring said digital signal from said ADC to said computer; and processing said digital signals in said computer in accordance with the type of said chemical sensor;

wherein said chemical sensor is not a chemical sensor used in amperometry and conductometry, wherein said transforming circuit is a voltage follower provided that the chemical sensor is a chemical sensor used in potentiometry, and wherein said computer is further provided with a Digital-to-Analog converter (DAC), and said DAC is connected to said chemical sensor by a Galvanostat circuit, wherein a Galvanostatic current is received by said chemical sensor from said Galvanostat circuit in cooperation with said DAC and said control computer program executed by said computer so that a potentiometry under Galvanostatic condition is carried out.

2. A system for collecting chemical signals comprising:

a computer for executing a control computer program;

at least one chemical sensor for providing output signals;

at least one transforming circuit for transforming said output signals received from said at least one chemical sensor into desired electronic signals, one end of said transforming circuit being connected with said at least one chemical sensor;

one or more Analog-to-Digital Converter (ADC) interface cards for converting said desired electronic signals into digital signals and transferring said digital signals to said computer, said ADC interface cards connecting a second end of said at least one transforming circuit with the computer;

wherein said at least one transforming circuit includes a voltage follower provided that said at least one chemical sensor is a chemical sensor used in potentiometry; or said at least one transforming circuit is a current-potential converter provided that said at least one chemical sensor is a chemical sensor used in amperomtery or conductometry, whereby said output signals from said at least one chemical sensor are converted into digital signals by using said at least one transforming circuit and said ADC in cooperation with said control computer program executed in said computer, and said digital signals are processed in said computer in accordance with the type of said chemical sensor, and wherein said at least one chemical sensor is a chemical sensor used in potentiometry, said computer is further provided with a Digital-to-Analog converter (DAC), and said DAC is connected to said one or more chemical sensors with a Galvanostat circuit so that a Galvanostatic current can be received by said at least one chemical sensor from said Galvanostat circuit in cooperation with said DAC and said control computer program executed in said computer, and thus potentiometry under a Galvanostatic condition can be carried out.

3. A system for collecting chemical signals comprising:

a computer for executing a control computer program;

at least one chemical sensor for providing output signals;

at least one transforming circuit for transforming said output signals received from said at least one chemical sensor into desired electronic signals, one end of said transforming circuit being connected with said at least one chemical sensor;

one or more Analog-to-Digital Converter (ADC) interface cards for converting said desired electronic signals into digital signals and transferring said digital signals to said computer, said ADC interface cards connecting a second end of said at least one transforming circuit with the computer;

wherein said at least one transforming circuit includes a voltage follower provided that said at least one chemical sensor is a chemical sensor used in potentiometry; or said at least one transforming circuit is a current-potential converter provided that said at least one chemical sensor is a chemical sensor used in amperomtery or conductometry, whereby said output signals from said at least one chemical sensor are converted into digital signals by using said at least one transforming circuit and said ADC in cooperation with said control computer program executed in said computer, and said digital signals are processed in said computer in accordance with the type of said chemical sensor, and wherein said at least one chemical sensor is a chemical sensor used in amperometry, said computer is further provided with a Digital-to-Analog converter (DAC), and said DAC is connected to said at least one chemical sensor with a potentiostat circuit so that a current having a desired electric potential wave form or a potentiostatic current can be received by said at least one chemical sensors from said potentiostat circuit in cooperation with said DAC and said control computer program executed in said computer, and thus voltammetry or an amperometry under a potentiostatic condition can be carried out.

4. A system for collecting chemical signals comprising:

a computer for executing a control computer program;

at least one chemical sensor for providing output signals;

at least one transforming circuit for transforming said output signals received from said at least one chemical sensor into desired electronic signals, one end of said transforming circuit being connected with said at least one chemical sensor;

one or more Analog-to-Digital Converter (ADC) interface cards for converting said desired electronic signals into digital signals and transferring said digital signals to said computer, said ADC interface cards connecting a second end of said at least one transforming circuit with the computer;

wherein said at least one transforming circuit includes a voltage follower provided that said at least one chemical sensor is a chemical sensor used in potentiometry; or said at least one transforming circuit is a current-potential converter provided that said at least one chemical sensor is a chemical sensor used in amperomtery or conductometry, whereby said output signals from said at least one chemical sensor are converted into digital signals by using said at least one transforming circuit and said ADC in cooperation with said control computer program executed in said computer, and said digital signals are processed in said computer in accordance with the type of said chemical sensor, and wherein said at least one chemical sensor is a chemical sensor used in conductometry, said computer is further provided with a Digital-to-Analog converter (DAC) which is connected to said at least one chemical sensor so that an alternating current can be received by said at least one chemical sensor from said DAC in cooperation with said control computer program executed in said computer, and thus conductometry can be carried out.

5. A system for collecting chemical signals comprising:

a computer for executing a control computer program;

at least one chemical sensor for providing output signals;

at least one transforming circuit for transforming said output signals received from said at least one chemical sensor into desired electronic signals, one end of said transforming circuit being connected with said at least one chemical sensor;

one or more Analog-to-Digital Converter (ADC) interface cards for converting said desired electronic signals into digital signals and transferring said digital signals to said computer, said ADC interface cards connecting a second end of said at least one transforming circuit with the computer;

wherein said at least one transforming circuit includes a voltage follower provided that said at least one chemical sensor is a chemical sensor used in potentiometry; or said at least one transforming circuit is a current-potential converter provided that said at least one chemical sensor is a chemical sensor used in amperomtery or conductometry, whereby said output signals from said at least one chemical sensor are converted into digital signals by using said at least one transforming circuit and said ADC in cooperation with said control computer program executed in said computer, and said digital signals are processed in said computer in accordance with the type of said chemical sensor, and wherein said at least one transforming circuit includes a voltage follower and a current-potential converter, and said at least one chemical sensor includes a chemical sensor used in potentiometry and a chemical sensor used in amperometry or conductometry; wherein one end of said current-potential converter is connected with said chemical sensor used in amperometry or conductometry, and one end of said voltage follower is connected with said chemical sensor used in potentiometry.

6. The system according to claim 5, in which said computer is further provided with a Digital-to-Analog converter (DAC), and said DAC is connected to said chemical sensor used in potentiometry with a Galvanostat circuit so that a Galvanostatic current can be received by said chemical sensor used in potentiometry from said Galvanostat circuit in cooperation with said DAC and said control computer program executed in said computer, and thus a potentiometry under Galvanostatic condition can be carried out.

7. The system according to claim 6, in which said at least one chemical sensor includes a chemical sensor used in potentiometry and a chemical sensor used in amperometry, and said DAC is further connected to said chemical sensor used in amperometry with a potentiostat circuit so that a current having a desired electric potential wave form or a potentiostatic current can be received by said chemical sensor used in amperometry from said potentiostat circuit in cooperation with said DAC and said control computer program executed in said computer, and thus a voltammetry or an amperometry under potentiostatic condition can be carried out.

8. The system according to claim 6, in which said at least one chemical sensor includes a chemical sensor used in potentiometry and a chemical sensor used in conductometry, and said DAC is further connected to said chemical sensor used in conductometry so that an alternating current can be received by said chemical sensor used in conductometry from said DAC in cooperation with said control computer program executed in said computer, and thus a conductometry can be carried out.

9. The system according to claim 5, in which said at least one chemical sensor includes a chemical sensor used in potentiometry and a chemical sensor used in amperometry, and said computer is further provided with a Digital-to-Analog converter (DAC), wherein said DAC is connected to said chemical sensor used in amperometry with a potentiostat circuit so that a current having a desired electric potential wave form or a potentiostatic current can be received by said chemical sensor used in amperometry from said potentiostat circuit in cooperation with said DAC and said control computer program executed in said computer, and thus a voltammetry or an amperometry under potentiostatic condition can be carried out.

10. The system according to claim 5, in which said at least one chemical sensor includes a chemical sensor used in potentiometry and a chemical sensor used in conductometry, and said computer is further provided with a Digital-to-Analog converter (DAC) which is connected to said chemical sensor used in conductometry so that an alternating current can be received by said chemical sensor used in conductometry from said DAC in cooperation with said control computer program executed in said computer, and thus a conductometry can be carried out.

* * * * *